US00PP13415P2

(12) United States Plant Patent
Slaughter et al.

(10) Patent No.: US PP13,415 P2
(45) Date of Patent: Dec. 24, 2002

(54) PEACH TREE NAMED 'BURPEACHSEVEN'

(75) Inventors: John K. Slaughter, Clovis, CA (US); Timothy J. Gerdts, Kingsburg, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 10/004,303

(22) Filed: Oct. 29, 2001

(51) Int. Cl.[7] ..... A01H 5/00

(52) U.S. Cl. ..... Plt./198

(58) Field of Search ..... Plt./198

*Primary Examiner*—Bruce R. Campell
*Assistant Examiner*—Susan B. McCormick
(74) *Attorney, Agent, or Firm*—Wells St. John P.S.

(57) ABSTRACT

A new and distinctive variety of peach tree denominated varietally as 'Burpeachseven', and which is characterized as to novelty by a date of maturity for commercial harvesting and shipment of, approximately July 24 to August 10 under the ecological conditions prevailing in the San Joaquin Valley of Central California.

1 Drawing Sheet

BOTANICAL CLASSIFICATION

*Prunus persica.*

VARIETY DENOMINATION

'Burpeachseven'.

BACKGROUND OF THE NEW VARIETY

The present relates to a new, novel and distinct variety of peach tree, which has been denominated varietally as 'Burpeachseven'. The 'Burpeachseven' Peach Tree produces an exceptionally high quality, firm, yellow fleshed freestone peach which matures in the later portion of the mid-season. Another unique aspect of the 'Burpeachseven' is that it exhibits exceptionally firm flesh which then extends storage life.

ORIGIN

The present peach tree was the result of an ongoing program of fruit and nut tree breeding. The purpose of this program is to improve the commercial selections of prunus, malus and regia species. To this end, both controlled and hybrid crosses are made each year in order to produce seedling populations from which improved progenies are evaluated and selected.

The seedling 'Burpeachseven' was originated by us in 1994, and chosen from a population of seedlings which resulted from a controlled cross of the unnamed peach, 'A48-70' (unpatented), used as the seed parent, and an unnamed nectarine, which was used as the pollen parent. Resulting seed from this cross were planted in the spring of 1995. The new variety was selected from among seedlings growing in experimental orchards near the city of Fowler, Calif., County of Fresno, in the Central portion of the San Joaquin Valley of California. The 'Burpeachseven' was marked for subsequent observation during the 1997–2000 fruit growing seasons. After the 1997 season, the 'Burpeachseven' peach tree was selected for advanced evaluation and repropagation.

ASEXUAL REPRODUCTION

The new variety 'Burpeachseven' was grafted onto two separate and existing 'Nemared' Peach rootstocks in February of 1998. The scionwood used in this asexual propagation was collected from the original seedling. This propagation was performed in the experimental orchards near the city of Fowler, Calif., as previously described. Fruit from the resulting propagation has been evaluated for both the 1999 and 2000 fruit seasons. These evaluations have clearly demonstrated that the repropagated trees are true to the fruiting and vegetative characteristics of the original seedling in all observable aspects.

SUMMARY OF THE VARIETY

The 'Burpeachseven' Peach is characterized as to novelty and is otherwise noteworthy by producing fruit which ripens in the later portion of the mid-season; is considered very high quality; and which is extremely firm; and has an attractive coloration; and exhibits an increased shelf life when compared to the commercial varieties currently available. In this regard, the present variety of peach tree bears fruit which are typically ripe for commercial harvesting and shipment in the fourth week of July, as the fruit is grown in the Central San Joaquin Valley. The 'Burpeachseven' Peach ripens 7–10 days before the seed parent 'A48-70', but the 'Burpeachseven' Peach is firmer, larger and has better shelf life than does the 'A48-70' Peach.

BRIEF DESCRIPTION OF THE DRAWING

The accompanying drawing is a color photograph of a characteristic twig bearing typical leaves; several leaves showing both the dorsal and ventral coloration, and several mature fruit showing their external coloration sufficiently matured for harvesting and shipment. Additionally, one fruit of the subject variety is dissected in the axial or suture plane to illustrate the flesh and stone characteristics thereof.

DETAILED DESCRIPTION

Referring more specifically to the pomological details of this new and distinct variety of peach tree, the following has been observed under the ecological conditions prevailing at orchards located near the town of Fowler, county of Fresno, state of California. All major color code designations are by reference to The R.H.S. Colour Chart (Third Edition) provided by The Royal Horticultural Society of Great Britain.

Tree:

*Size.*—Generally — Considered neither excessively vigorous nor excessively weak when compared to other common commercial peach cultivars ripening in the mid season of maturity.

*Productivity.*—Productive.

*Figure.*—The 'Burpeachseven' Peach has been trained in central leader configuration but exhibits a generally upright to slightly spreading tropism when compared to average commercial available varieties of peach.

*Height.*—The 'Burpeachseven' Peach tress had a height dimension of 3.19 meters, after pruning, at the end of the 2000 growing season.

*Width.*—The 'Burpeachseven' Peach tree had a width 2.19 meters, after pruning, at the end of the 2000 growing season.

*Current season growth.*—The current season growth for the new variety was approximately 0.91–1.12 meters.

*Regularity of bearing.*—Regular, and considered hardy under typical Central San Joaquin Valley conditions.

Trunk:

*Diameter.*—Approximately 19.05 cm in diameter when measured at a distance of approximately 15.25 cm above the soil level, at the end of the 2000 growing season.

*Bark texture.*—Considered moderately rough with numerous folds of papery scarf skin being present.

*Lenticels.*—Numerous flat, oval lenticels are present. The lenticels range in size from approximately 2.0 to 6.0 millimeters in width, and from 1 to 2 millimeters in height.

*Lenticel color.*—Considered an Orange Brown. (RHS Greyed-Orange 171 A).

*Bark coloration.*—Variable, but it is generally considered to be a grey-brown (RHS Greyed-Orange Group 175B).

Branches:

*Size.*—Considered medium for the variety.

*Diameter.*—Average as compared to other varieties. The branches have a diameter of about 45.0 millimeters when measured during the third year after grafting.

*Surface texture.*—Average, and appearing furrowed on wood which is several years old.

*Crotch angles.*—Primary branches considered variable between about 44 to 49 degrees from the horizontal axis. This is not distinctive of the variety, however.

*Current season shoots.*—Surface texture — Substantially glabrous.

*Internode length.*—Approximately 2.1 to 2.3 cm.

*Color of mature branches.*—Medium brown, (RHS Grey Brown Group N199C).

*Current seasons shoots.*—Color — Light green, (RHS Yellow Green Group 144C). The color of new shoot tips is considered a bright and shiny green (RHS Green Group 134C).

Leaves:

*Size.*—Considered moderately large for the species. Leaf measurements have been taken from vigorous upright current season growth approximately at mid-shoot.

*Leaf length.*—Approximately 155 to 170 millimeters.

*Leaf width.*—Approximately 33 to 37 millimeters.

*Leaf thickness.*—Approximately 1 to 2 millimeters.

*Leaf base shape.*—Slightly oblique relative to the leaf longitudinal axis.

*Leaf form.*—Lanceolate.

*Leaf tip form.*—Acuminate.

*Leaf upper color.*—Dark green, (RHS Green Group 136/A).

*Leaf texture.*—Glabrous.

*Lower color surface.*—Medium green, (RHS 138/B).

*Leaf venation.*—Pinnately veined.

*Mid-vein.*—Color — Light yellow green, (RHS Yellow Green Group 149 B to 144 B).

*Leaf margins.*—Form — Considered crenate, occasionally doubly crenate. Uniformity — Considered generally uniform.

*Leaf petioles.*—Size — Considered medium long to long. Length — Approximately 9–12 mm. Diameter — Approximately 1.5 to 2.5 mm. Color — Pale green, (RHS Yellow Green Group 144 B).

*Leaf glands.*—Size — Approximately 1 mm in height and 1 to 2 mm in width. Numbers — Generally one per side, occasionally two per side. Type — Globose, considered reasonably unappressed at the petiole margin. Color — Greenish brown (RHS Yellow Green Group152 B).

*Leaf stipules.*—Size — Medium for the variety. Number — Typically 2 per leaf bud and up to 6 per shoot tip. Form — Lanceolate in form and having a serrated margin. Color — Green (RHS Green Group 132 A) when young but graduating to a yellow-brown color (RHS Grey Orange group 177 A) with advancing senescence. The stipules are considered to be early deciduous.

Flowers:

*Flower buds.*—Generally — The floral buds are considered to be medium to medium large (11 millimeters wide) and (15 millimeters long) in size, conic in form, and slightly appressed relative to the bearing shoot.

*Flower buds.*—Color — The bud scales are gray-brown, (approximately RHS Grey Orange Group 177 D). The buds are considered hardy under typical central San Joaquin Valley climatic conditions.

*Hardiness.*—No winter injury has been noted in the several years of evaluation in the Central San Joaquin Valley. The current variety has not been intentionally subjected to drought or heat stress and therefore this information is not available.

*Date of first bloom.*—Mar. 3$^{rd}$, 1999.

*Blooming type.*—Considered neither early nor late in relation to other peach commercial cultivars commonly growing in the central San Joaquin Valley. Date of full bloom was Mar. 8, 1999.

*Duration of bloom.*—Approximately 9 days.

*Flowers type.*—The variety is considered to be a showy type flower.

*Flower size.*—Flower diameter at full bloom is approximately 42 to 46 millimeters.

*Bloom quantity.*—Considered abundant.

*Flower bud frequency.*—Normally 1 to 2 appear per node.

*Petal size.*—Generally — Considered medium large to large for the species. Length — Approximately 18 to 22 millimeters. Width — Approximately 16 to 19 millimeters.

*Petal form.*—Broadly ovate.

*Petal count.*—Nearly always 5.

*Petal texture.*—Glabrous.

*Petal color.*—Light pink when young, (RHS Red Purple Group 68 D), and darkening with advanced senescence to a medium pink (RHS Red Purple Group 68 B).

*Fragrance.*—Slight.

*Petal claw.*—Form — The claw is considered truncate in shape and has a medium-large size when compared to other varieties. Length — Approximately 2 to 4 millimeters. Width — Approximately 4 to 6 millimeters.

*Petal margins.*—Generally considered variable, from nearly smooth, to moderately undulate and ruffled, especially apically.

*Petal apex.*—Generally — The petal apices appear slightly domed.

*Flower pedicel.*—Length — Considered medium-long, and having an average length of approximately 3 to 5 millimeters. Diameter — Considered average, approximately 2 to 3 millimeters. Color — A medium green (RHS Yellow-Green Group 152 A).

*Floral nectaries.*—Color — Dull orange to orange-gold (RHS Greyed-Red Group 179 A).

*Calyx.*—Surface Texture — Generally glabrous. Color — A dull red, (approximately RHS Greyed-Red Group 181 B).

*Sepals.*—Surface Texture — The surface of the sepals has a short, fine, wooly and a gray colored texture. Size — Average, and ovate in form. Color — A dull red, (approximately RHS Greyed-Red Group 182 B).

*Anthers.*—Generally — Average to above average in length. Color — Red to reddish-orange dorsally, (approximately RHS Greyed Purple Group 184 B).

*Pollen production.*—Pollen is abundant, and has a yellow-golden color, (approximately RHS Yellow Orange Group 19 A).

*Filaments.*—Size — Variable in length, approximately 15 to 18 millimeters in length. Filaments are slightly longer than the pistil. Color — White, (RHS Red Purple Group 69 D), and darkening with advanced maturity.

*Pistil.*—Generally — Average in size. Length — Approximately 16 to 20 millimeters including the ovary. Color — Considered a very pale green when young, (approximately RHS Yellow Green Group 150 D), and becoming slightly more yellowish with advancing maturity. Surface texture — The variety has a long, pale green to whitish-yellow pubescent pistil.

Fruit:

*Maturity when described.*—The present variety of fruit is described, as it would be found in its ripe condition at full commercial maturity. In this regard, the fruit of the present variety was first picked on Jul. 24, 1999. The date of last pick of the same variety in 1999 was approximately August 9 under the ecological conditions prevailing in the San Joaquin Valley of Central California.

*Size.*—Generally — Medium large, and considered uniform.

*Average cheek diameter.*—Approximately 76 to 79 millimeters.

*Average suture diameter.*—Approximately 73 to 74 millimeters.

*Average axial diameter.*—Approximately 77 to 80 millimeters.

*Typical weight.*—Approximately 248 grams.

*Fruit form.*—Generally — Oblate in its lateral aspect. The fruit is generally uniform in symmetry with a slightly oval form when viewed from the apical aspect.

*Fruit suture.*—Generally — The suture appears as a thin line which extends from the base of the apex, and appears slightly deeper basally, within the stem well, and apically on both sides of the pistil point. No apparent callousing or stitching exists along the suture line.

*Suture.*—Color — The suture normally is the same color as the underlying blush and the adjoining skin surface. Both the orange-yellow background, (approximately RHS Yellow-Orange Group 19/A to 11/D) and the red orange color (approximately RHS Red Orange-Group 46/A) occur.

*Ventral surface.*—Form — Considered uniform.

*Stem cavity.*—Size — Considered moderately shallow for the species. Width — Approximately 8–12 millimeters. Length — Approximately 19–25 millimeters. Depth — Approximately 6 to 9 millimeters. Form — Considered narrowly oval.

*Fruit base.*—Generally — Considered truncate in form, and uniform.

*Fruit apex.*—Generally — Considered depressed and usually recessed below the height of the apical shoulders.

*Fruit stem.*—Generally — Considered medium to medium long in length, approximately 7 to 10 millimeters. Diameter — Approximately 3 to 4 millimeters. Color — Generally a pale yellow-green (approximately RHS Yellow Green Group 145/B).

*Fruit skin.*—Generally — Considered average in thickness. Surface Texture — The variety has a very short pubescence. Skin Acidity — Considered neutral. Tenacious to Flesh — Yes at commercial maturity. Tendency to Crack — Not observed.

*Skin color.*—Generally — Variable, with approximately 80% to 90% of the fruit surface covered with an attractive red blush.

*Blush color.*—The blush color is generally more prevalent apically. This red blush color ranges from a dark red, (approximately RHS Red Group 47/B to 46/A) to an orange red, (approximately RHS 47/C to 33B), with many degrees of shading and blending occurring between these colorations.

*Skin ground color.*—This is generally present in variable percentages covering approximately 10% to 20% of the fruit's surface. The skin ground color is a yellow-golden (approximately RHS Yellow Orange Group 19/A to 11/D).

*Flesh color.*—Generally — Considered variable from yellow orange, (approximately RHS Yellow Orange Group 21/B to 18/A) to a reddish orange, (approximately RHS Red Group 44/C). The variable color can radiate into the flesh beginning at the exterior margin.

*Flesh fibers.*—Generally — Present, moderately numerous and lightly colored. These fibers are present throughout the flesh.

*Stone cavity.*—Color — Red, (approximately RHS Red Orange Group 46/B) to a yellow color, (approximately RHS Yellow Group 18/B). With increasing maturity, occasional red flecks can appear randomly in the flesh. These red flecks are approximately the same color of red as displayed at the stone cavity. The stone cavity is described as free, and fine. The flesh margin defining the stone cavity completely separates from the stone, but the typical large, spacious vacuole, that is found in most freestones, does not develop in the current variety giving it a free but close stone cavity margin.

*Flesh texture.*—Generally — The flesh is considered very firm, fine and quite dense at commercial maturity.

*Ripening.*—Generally — The fruit of the current variety ripens evenly.

*Flavor.*—Considered sweet and mildy acidic. The flavor is considered both pleasant and balanced.

*Aroma.*—Pleasant and moderately abundant.

*Eating quality.*—Generally — Considered very good and well above average when compared to common varieties maturing in the same season.

Stone:

*Attachment.*—Generally — Freestone at commercial maturity.

*Stone size.*—Generally — Considered medium for the variety. Length — Approximately 34 to 36 millimeters. Width — Approximately 27 to 29 millimeters. Diameter — Approximately 20 to 22 millimeters.

*Fibers.*—Generally — A few medium length fibers are attached along the surface of the stone.

*Stone form.*—Generally — The stone is considered oval.

*Stone base.*—The stone is somewhat oblique.

*Base angle.*—The base angle of the stone is variable, but, most frequently is considered slightly oblique to the stone axis.

*Hilum.*—Generally — Considered medium in size, and relatively well defined. The hilum is approximately 5 to 7 millimeters long and approximately 4 to 5 millimeters wide.

*Form.*—Considered oval.

*Apex.*—Shape — The stone apex is raised and has an acute tip.

*Stone shape.*—Considered slightly variable. The stone is normally nearly equal, although occasionally may appear more unequal.

*Stone surface.*—Surface Texture — Generally considered medium in roughness and exhibits substantial pitting laterally. Substantial grooving is apparent over the apical shoulders. Surface pitting is prominent, generally, and more frequently, it is present basally. Ridges — Numerous fine ridges are present basally, and converge towards the base of the stone. Ventral Edge — Width — Considered medium, and having a dimension of approximately 5 to 6.5 millimeters at the mid-suture and wings most prominent over the basal area. Dorsal Edge — Shape — Full, heavily grooved, and having jagged edges. The dorsal edge is moderately eroded over the apical shoulder.

*Stone color.*—The color of the dry stone is a light to medium brown, (approximately RHS Orange Red Group 34 C).

*Tendency to split.*—Very infrequent splitting was noted.

*Kernel.*—Form — Oval when the fruit is ripe. Length — about 18–21 mm. Width — about 12–14 mm. Pellicle — Slight pubescence is present. Color — (RHS Greyed Orange Group 172 A).

*Use.*—The subject variety 'Burpeachseven' is considered to be a peach tree of late mid-season maturity, and which produces fruit which are viry firm, attractively colored, and which are useful for both local and long distance shipping.

*Keeping quality.*—Excellent. Fruit has stored well up to 25 days after harvest at 1.0 degrees Celsius.

*Resistance to insects and disease.*—No particular susceptibilities were noted.

*Shipping quality.*—Well above average.

Although the new variety of peach tree possesses the described characteristics when grown under the ecological conditions prevailing near Fowler, Calif., in the central part of the San Joaquin Valley of California, it will be understood that variations of the usual magnitude and characteristics incident to changes in growing conditions, fertilization, pruning, pest control and horticultural management are to be expected.

Having thus described and illustrated our new variety peach tree, what we claim is new and desire to secure by Plant Letters Patent is:

1. A new distinct variety of peach tree substantially as illustrated and described and which is characterized principally as novelty by producing an attractively colored freestone Peach which is mature for harvesting and shipment approximately July 24 to August 9 under the ecological conditions prevailing in the San Joaquin Valley of Central California.

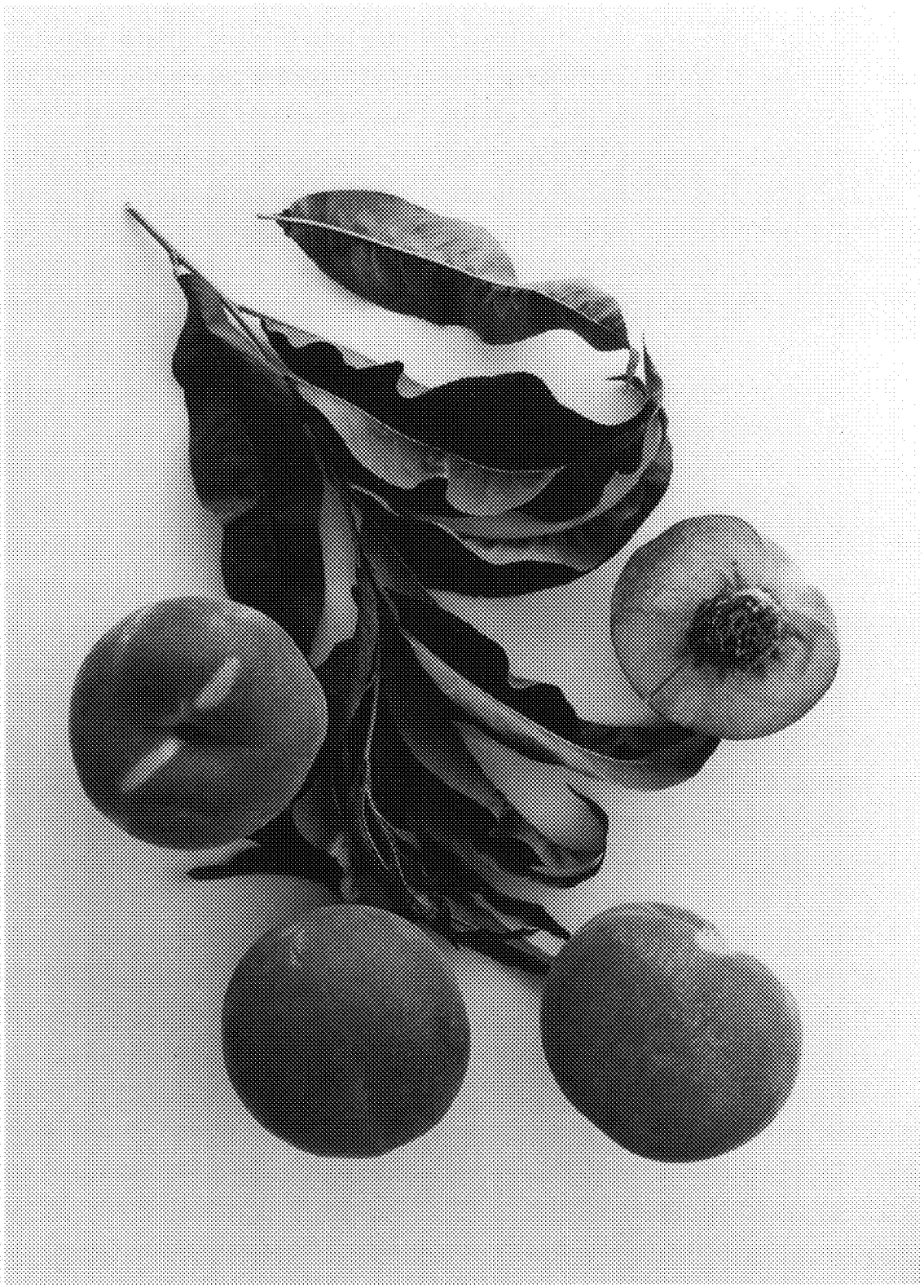

* * * * *